United States Patent
Gubachy

(10) Patent No.: US 11,497,649 B2
(45) Date of Patent: Nov. 15, 2022

(54) INTRACANALICULAR DISSOLVABLE PUNCTUM PLUG INSERTER

(71) Applicant: AlphaMed, Inc., El Paso, TX (US)

(72) Inventor: James Michael Gubachy, El Paso, TX (US)

(73) Assignee: ALPHAMED, INC., El Paso, TX (US)

(*) Notice: Subject to any disclaimer, the term of this patent is extended or adjusted under 35 U.S.C. 154(b) by 798 days.

(21) Appl. No.: 16/360,287

(22) Filed: Mar. 21, 2019

(65) Prior Publication Data
US 2019/0290488 A1 Sep. 26, 2019

Related U.S. Application Data

(60) Provisional application No. 62/646,538, filed on Mar. 22, 2018.

(51) Int. Cl.
*A61F 9/007* (2006.01)
*A61F 9/00* (2006.01)

(52) U.S. Cl.
CPC ........ *A61F 9/00772* (2013.01); *A61F 9/0017* (2013.01); *A61F 2230/0067* (2013.01); *A61F 2230/0069* (2013.01)

(58) Field of Classification Search
CPC ............... A61F 9/00772; A61F 9/0017; A61F 2230/0067; A61F 2230/0069
See application file for complete search history.

(56) References Cited

U.S. PATENT DOCUMENTS

| | | | |
|---|---|---|---|
| 5,669,501 A | 9/1997 | Hissong et al. | |
| 5,921,990 A | 7/1999 | Webb | |
| 8,591,484 B2 | 11/2013 | Gubachy et al. | |
| 2004/0068235 A1* | 4/2004 | Hallam | A61F 2/0095 606/191 |
| 2004/0068286 A1* | 4/2004 | Mendius | A61B 17/12159 606/191 |
| 2007/0243230 A1 | 10/2007 | de Juan, Jr. et al. | |
| 2009/0105749 A1 | 4/2009 | De Juan et al. | |
| 2009/0281520 A1 | 11/2009 | Highley et al. | |
| 2011/0009874 A1 | 1/2011 | Wardle et al. | |
| 2013/0013207 A1 | 1/2013 | Frejvall | |
| 2013/0023837 A1* | 1/2013 | Becker | A61F 9/00772 604/294 |

(Continued)

FOREIGN PATENT DOCUMENTS

GB 2548987 A 10/2017

*Primary Examiner* — Camtu T Nguyen
(74) *Attorney, Agent, or Firm* — D'Ambrosio & Menon, PLLC; Usha Menon

(57) ABSTRACT

Devices and methods for inserting a pre-loaded intracanalicular plug for the treatment of dry eyes. In one embodiment, an intracanalicular plug inserter device includes: (a) an elongate body having a longitudinal axis, the body having: an inserter end, wherein the inserter end has an opening therein; and a distal end, wherein the distal end is longitudinally opposing the inserter end; and (b) a plug ejector, wherein the plug injector comprises: a slider; and a rod coupled to a first end of the slider, wherein the plug ejector is configured to be moveable between a first position adjacent an opening in the inserter end and a second position that is further from the opening. The plug is mounted within the body and abuts first end of the rod adjacent the opening in the inserter end.

9 Claims, 5 Drawing Sheets

(56) References Cited

U.S. PATENT DOCUMENTS

2014/0243763 A1 8/2014 Heikali
2015/0065940 A1 3/2015 Rangel-Friedman et al.
2017/0172797 A1 6/2017 Horvath et al.

* cited by examiner

INTRACANALICULAR DISSOLVABLE PUNCTUM PLUG INSERTER

CROSS REFERENCE TO RELATED APPLICATION

This application claims the benefit of Provisional U.S. Patent Application No. 62/646,538, filed Mar. 22, 2018, and entitled "INTRACANALICULAR DISSOLVABLE PUNCTUM PLUG INSERTER", the entire content and disclosure of which, both express and implied, is incorporated herein by reference.

TECHNICAL FIELD

The invention relates generally to devices and methods for the treatment of dry eyes.

BACKGROUND

Dry eye syndrome affects millions of people each year, causing discomfort, redness, corneal irritation, and contact lens intolerance. Tears normally drain by passing through two lacrimal orifices or puncta (upper and lower) on the medial surface of each eyelid, then through vertical and horizontal canaliculi into the nasal cavity. Dry eye syndrome can be treated by occluding the puncta using punctal occluders or by placing implants into the canaliculi.

Plugs are very tiny, biocompatible devices that can be used to treat dry eyes. There are two common types of plugs depending on their location. Surface plugs sit at the surface of the tear duct and they may be visible just outside the tear duct. Canalicular or intracanalicular plugs, on the other hand, are placed deep inside/within the canaliculus (either the vertical or the horizontal canaliculus).

Currently, intracanalicular plugs are pushed or inserted into the canaliculi using a pair of forceps. This procedure is very cumbersome—for example, an eye doctor (such as, an optometrist, ophthalmologist or another eye care professional), while performing a slit-lamp examination, has to first open a package containing the canalicular plug. This is followed by picking up and inserting the plug into the canaliculus using forceps. Since the plug is a tiny device, it presents a likely scenario where the eye doctor inadvertently drops the plug before it is inserted into the canaliculus. Some eye doctors may also lack the experience to perform the procedure and may be intimidated when trying to insert the plug into the canaliculus because of its small size.

U.S. Pat. No. 8,591,484 discloses a device for inserting a surface plug. The device includes a metal or plastic wire or any other wiring capable of being flexed. The plug is positioned at a tip of the wire. The wire is embedded within a trough having a backstop for holding the wire in place. An adhesive is applied to the area of contact between the wire and the trough for holding the wire in place. When a button is depressed, it applies a downward force on the wire proximate the backstop. Because one end of the wire is held in place at the backstop, the downward force applied by the button produces a tensile force on the wire, pulling it inwards. Complete depression of the plug ejector causes the withdrawal of the tip of the wire from the plug, thereby releasing the plug. A drawback with the device is that it involves the use of a wire for holding the plug. The patented device is configured for the placement of a surface plug. Since the device is not configured to enter the opening of the canaliculus, it will not push the plug into the canaliculus.

Accordingly, there is a need for a convenient device that can facilitate the placement of an intracanalicular plug into the canaliculus without using forceps or without the use of insertion devices that include wires for holding the plug. Ideally, the device is provided with pre-loaded plugs and does not rely on the eye doctor to load them onto the device.

SUMMARY

The present invention involves a device for inserting an intracanalicular plug into the canaliculus and methods for treatment of dry eyes. The plug may be made of a suitable biocompatible material, such as, polydioxanone or any other suitable material. Conveniently, the plug can be pre-loaded (or pre-mounted) on the device.

The present invention facilitates a one-step treatment process for inserting the plug into the canaliculus to temporarily restrict the natural lubricating tears from draining off the eye by using a single device that is pre-loaded with a dissolvable intracanalicular plug. This avoids the need for an eye doctor to remove the plug from separate package and eliminates the cumbersome process of using forceps to hold and insert the plug into the canaliculus or punctum. Advantageously, even eye doctors with little or no experience are able to easily insert the dissolvable punctum plugs into the canaliculus. The treatment can be used for long-term treatment of certain eye conditions commonly referred to as dry eye syndrome, as well as the dry eye component of ocular surface diseases and other conditions of tear insufficiency.

In one embodiment, an intracanalicular plug inserter device includes: (a) an elongate body having a longitudinal axis, the body having: an inserter end, wherein the inserter end has an opening therein; and a distal end, wherein the distal end is longitudinally opposing the inserter end; and (b) a plug ejector, wherein the plug injector comprises: a slider; and a rod coupled to a first end of the slider, wherein the plug ejector is configured to be moveable between a first position adjacent an opening in the inserter end and a second position that is further from the opening. The plug is mounted within the body and abuts first end of the rod adjacent the opening in the inserter end. The rod is configured to eject the plug from the opening in the inserter end when the first end of the slider is moved toward the inserter end. The plug ejector further includes a depressible button having a first (upper) side positioned outside of the body and a second side mounted on the slider. The button is flanked by a first sidewall and a second sidewall. The second (base) side of the button includes a pair of legs which are clipped to a first arm of the slider. The button is substantially locked in a first position by a locking means that includes a protrusion and an indentation on the first arm of the slider. The protrusion is adjacent the first sidewall. The button is configured to be moved along the longitudinal axis of the body from its first position to a second position adjacent the second sidewall by depressing the button to release it from the indentation and then sliding it along the slide toward the second position. The device further includes a removable cap fitted to cover plug mounted at the inserter end of the body. The device also includes integral means for dilating a lacrimal punctum disposed at the distal end of the body. The means for dilating the punctum comprises a fine tip.

In another embodiment, a kit comprising the intracanalicular plug inserter device is provided. The kit further includes a tray for receiving the device and instructions for using the device.

In yet another embodiment, a method of assembling an intracanalicular plug inserter device is disclosed. The method involves providing an intracanalicular plug; mounting the intracanalicular plug within the intracanalicular plug inserter device and compressing a cap on the inserter end of the device to hold the intracanalicular plug securely in position on the device. The method also involves sealing the device in a pre-molded tray with a sterile barrier lid. The method further comprises subjecting the tray to sterilization.

In another embodiment, a method of treating dry eyes involves providing the intracanalicular plug inserter device disclosed herein; inserting the inserter end of the device into a patient's canaliculus; and actuating the plug ejector of the device to cause the plug to be ejected out of the opening at the inserter end. The method further comprises dilating the patient's punctum prior to inserting the plug. The distal end of the device can be used to push the plug further into the canaliculus.

DETAILED DESCRIPTION

The term and phrases "invention," "present invention," "instant invention," and similar terms and phrases as used herein are non-limiting and are not intended to limit the present subject matter to any single embodiment, but rather encompass all possible embodiments as described.

The device and methods described herein can "comprise," "consist essentially of," or "consist of" any of the features or steps disclosed throughout the specification. As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and can include the features and steps of the present invention and do not exclude other features or steps described herein. The use of the word "a" or "an" when used in conjunction with the term "comprising" in the claims and/or the specification may mean "one," but it is also consistent with the meaning of "one or more," "at least one," and "one or more than one." As used herein, "consisting essentially of" means that the invention may include features or steps in addition to those recited in the claim, but only if the additional features or steps do not materially alter the basic and novel characteristics of the claimed invention.

All ranges recited herein include the endpoints, including those that recite a range "between" two values. Terms such as "about," "generally," "substantially," and the like are to be construed as modifying a term or value such that it is not an absolute. Such terms will be defined by the circumstances and the terms that they modify as those terms are understood by those of skill in the art. The term "substantially" and its variations are defined as being largely but not necessarily wholly what is specified as understood by one of ordinary skill in the art, and in one non-limiting embodiment substantially refers to ranges within 0.5%-5%.

Figure 1A:
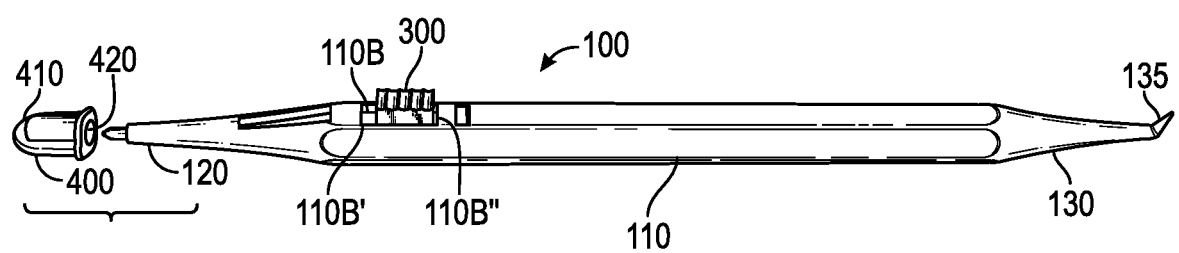
FIGS. 1A-1C illustrate various views of an intracanalicular plug inserter device in accordance with one or more embodiments of the invention.
Figure 1B:
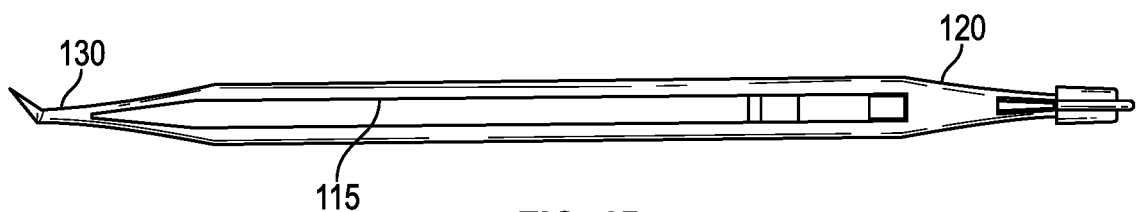
Figure 1C:
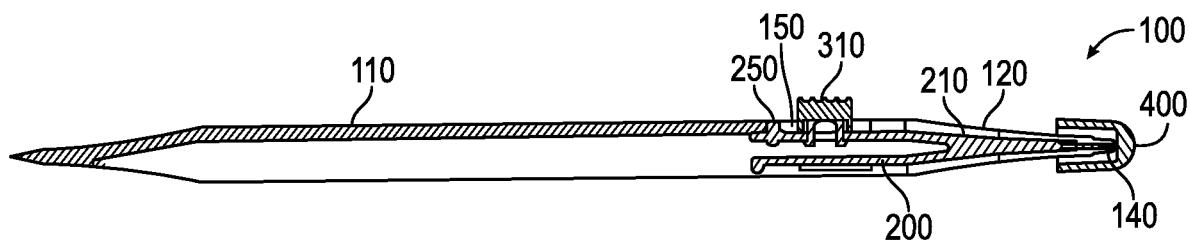

FIGS. 1A-1C illustrate different views of embodiment of a device 100 for inserting a pre-loaded intracanalicular plug (referred to interchangeably as "plug" hereinafter) for the treatment of dry eyes. The device 100 is configured as a single-use inserter tool for the plug 140. The plug 140 is configured to temporarily restrict natural lubricating tears from draining off from the eye. The device 100 also has an integral dilator tip/end 135. The device 100 has an ergonomic design and is pencil-sized for ease of handling. In certain embodiments, the device 100 can be between 5 cm-25 cm in length. Also, similar to a pencil, the device 100 can be held and manipulated between the thumb, forefinger and a side of the middle finger of one hand by a user. The lightweight, handheld device 100 is convenient to use and it facilitates efficiency and cost-savings which may ultimately be passed down to the patients.

The device 100 can be manufactured from stainless steel, polycarbonate, plastic, any combination of these, or another suitable material. The device 100 includes an elongate housing or body 110, wherein the body has an inserter end ("first end") 120 and a distal end ("second end") 130 longitudinally opposing the inserter end, and a plug ejector 200 mounted inside the body. The plug ejector 200 is configured with an integral slider 210 and a button 300 to eject a pre-loaded intracanalicular plug 140 into the canaliculus. The device 100 further includes a cover or cap 400 for protecting the plug 140 within the inserter end 120.

The elongate body 110 has a substantially longitudinal axis. A first end of the body 110 terminates in a plug inserter end 120 while a second end of the body terminates in a dilator tip 135. The body 110 can have raised ridges, scoring, or a roughened surface to facilitate a stable grip in the hands of an eye doctor. In one or more embodiments, the body 110 may have a hexagonal cross-section. In other embodiments, the body 110 may have a circular or polygonal cross-section. Optionally, a bottom portion of the body 110 may include an elongate groove 115. The groove 115 may extend from substantially a first end 120 of the body to substantially a second end 130 of the body. The groove 115 ensures that the device 100 is light weight and it can also facilitate the insertion of the plug ejector 200 and the plug 140 during the manufacture/assembly process. The body 110 may have a larger diameter toward its middle or it may have a uniform diameter.

The plug 140 may be made of a biocompatible material. Preferably, the plug may be formed from a water-soluble, dissolvable material, such as collagen, or a polydioxanone plug, however, it can also include other types of dissolvable plugs that are medically-compatible and made of a suitable material. In some embodiments, the plug 140 is opaque and cylindrical in shape. The plug 140 is designed to fit snugly inside the canaliculus to block the flow of tears. Since the punctal diameter of most patients is around 0.4 mm-0.5 mm in diameter, a typical plug will range between about 0.4 mm to about 0.5 mm in diameter as well. Consequently, once the plug has been inserted, the tears can stay on the surface of the eye for a longer duration which in turn, ensures natural lubrication of the eye. As a result, the eye stays moist and comfortable.

A first end 120 of the body is configured for inserting a plug into the canaliculus. The plug inserter end 120 includes an inserter tip 125. The inserter tip 125 is configured to firmly retain the plug 140. In one non-limiting embodiment, as shown in FIGS. 2A-2D, the inserter tip 125 has a "crimp"-type design. For instance, the inserter tip 125 involves a substantially silo- or conical-shaped portion 125A, a channel 125B that tapers inward and an opening 127. The channel 125B provides a close fit to the outer surface of the plug 140 and it is configured to frictionably hold the plug 140 until it is ejected from opening 127. The diameter of the opening 127 may be adjusted to substantially match that of the plug 140.

As shown in FIGS. 1A and 1C, the device 110 further includes a cover or cap 400. The cap 400 protects the plug 140 at the inserter tip 125. The cap 400 includes a dome-shaped housing 410 and an opening 420 for receiving the plug and inserter tip 125. The cap 400 may be made of polycarbonate polymer or any other suitable material. The cap 400 is configured to snap on the inserter tip 125. In certain embodiments, the cap includes a compression means for compressing the plug 140 to about a $1000^{th}$ of an inch.

A cross-sectional view of the plug ejector 200 is shown in FIG. 1C. The plug ejector 200 includes an integral slider 210 and an ejector means 300. The slider 210 is mounted within the longitudinal groove 115 of the body 110. The slider 210 has a first arm 210A and a second arm 210B which are separated by an opening 210D at a first end. The arms 210A, 210B are coupled together at a tapering second end 210C. The slider 210 is configured to be flexed (that is, it is not made of a rigid material). The two arms 210A, 210B of the slider can be flexed toward a midline of the slider when it is inserted into the body 110 during the assembly of the device 110. The arms 210A, 210B are configured to flex back (away from the midline) to their original position once the slider is inserted within the body 110.

The plug ejector 200 further includes a plunger or rod 220. A first end 230 of the rod 220 is affixed to the second end 210C of the slider. The opposing end 240 of the rod 220 is configured to abut a first end of the plug 140 (as shown in FIG. 1C) inside the channel 125B. Advantageously, the rod 220 is precision molded such that it can fit inside the channel 125B. A second end of the plug 140 is configured to slightly extend out from the opening 127 of the inserter tip.

Figure 4:
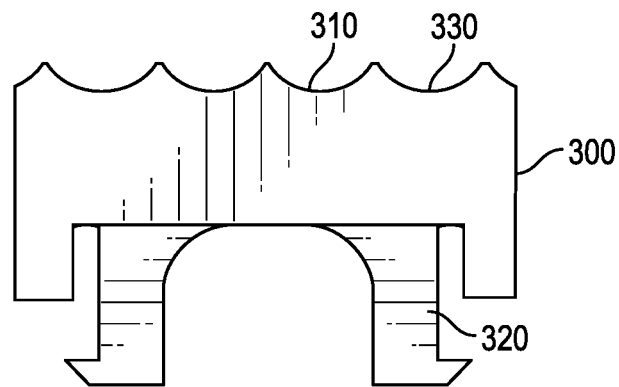
FIG. 4 illustrates a button in accordance with one or more embodiments of the invention.

The plug ejector 200 further includes an ejector means 300. As further shown in FIGS. 4 and 5, the ejector means 300 can include a button 310 or any other suitable mechanism such as, a lever. The button 310 is interposed on an upper portion of the body 110 and it can be configured to have any suitable shape. In one embodiment the base of the button includes a pair of legs 320. The legs 320 are clipped to the first arm 210A of the slider through slots 215. A raised portion 330 of the button protrudes outwardly from an upper portion of the body. The raised portion 330 can include ridges or grooves for facilitating a stable grip. The button 310 can be located within a channel 110B on an upper portion of the body 110. The channel 110B is flanked by sidewalls 110B' and 110B". The button 310 is locked in a first position by sidewall 110B" by the interaction of a locking means, such as, protrusion 250 and an indentation 150 of the first arm 210A. The button 310 is originally compressed in position. To release the button 310, it can be depressed to remove the protrusion 250 from the indention 150, and it can be then moved from the first position to a second position proximal to the opposing sidewall 110B' or to any position therebetween within the channel 110B.

Figure 5:
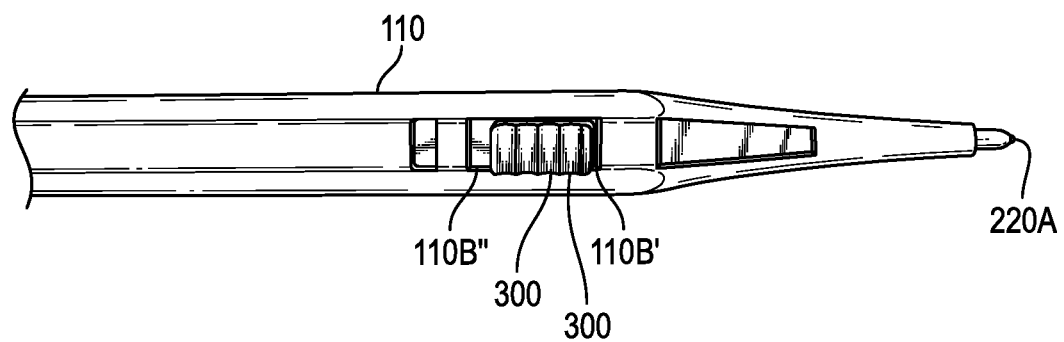
FIG. 5 illustrates another view of the device with the button according to an embodiment of the invention.

In use, the eye doctor can actuate the plug ejector 200 by gently depressing the top/raised portion 330 of the button to release it from its locked position. Pressing the top of the button 330 forces the base 320 of the button to push the first slider arm 210B toward the second slider arm 210B. The button 300 can then be moved along the axis of the body 110 from a first position along sidewall 110B" to a second position along sidewall 110B'. This causes the slider arms 210A and 210B and the rod 220 to slide forward toward the opening 127 at the inserter end. The rod 220 moves the plug 140 through the channel 125B and ejects it out from the opening 127 into the canaliculus. The tip 220A of the rod has a slightly smaller diameter in comparison to the opening 127. As shown in FIG. 5, after the plug 140 has been ejected, a small portion of the tip 220A of the rod may protrude through the opening 127.

The rod 220 is configured to be retractable and can slide back within the body 110 when the button 300 is pushed backward (that is, when the button is moved away from the inserter tip). The inserter end can also include a collar. The collar may be cushioned to facilitate a firm grip.

Figure 2A:
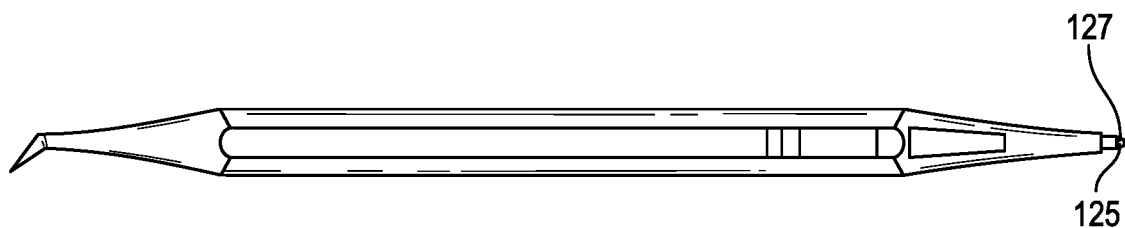
FIGS. 2A-2E illustrate various views of the device and its components in accordance with one or more embodiments of the invention.
Figure 2B:
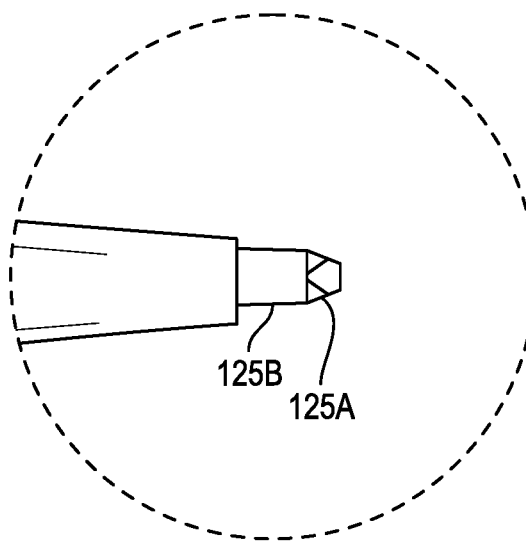
Figure 2E:
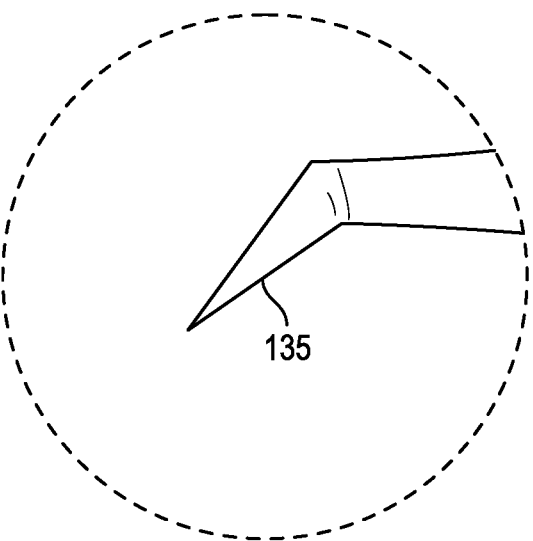
Figure 2C:
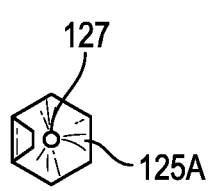
Figure 2D:
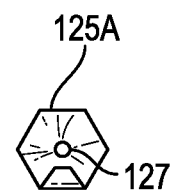
Figure 3:
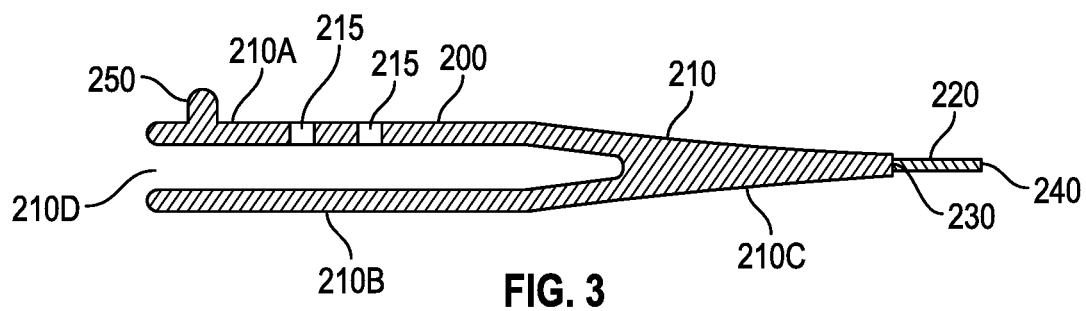
FIG. 3 illustrates a slider in accordance with one or more embodiments of the invention.

A distal end 130 of the body is located longitudinally opposite the inserter end 120. As shown in FIGS. 1A and 2E, the distal end 130 can taper into a very small and fine tip/point 135. The tip 135 may be angled with respect to the longitudinal axis of the body 110. For example, the tip 135 may be configured to point upward or downward. In certain embodiments, the tip can also have a longitudinal axis substantially coincident with the longitudinal axis of the body 110.

In some instances, the patient's punctum may have to be dilated prior to inserting a plug. Dilation may involve the use of forceps or other specialized dilation tools. This adds to the complexity/cumbersomeness and expense of the treatment procedure.

The tip 135 can be conveniently used to dilate the lacrimal punctum. The size and shape of the dilator tip 135 can be customized. For instance, the size of the dilator tip 135 can be customized to approximate the punctal diameter. Accordingly, the device 100 combines a means for inserting a pre-loaded plug into the punctum with a means for dilating the punctum. Conveniently, the tip 135 can also be configured to push the inserted plug further into the canaliculus after it has been ejected into the canaliculus by the device.

It is understood, however, that while a combination of a dilator and inserter eliminates the wasteful use of multiple devices during the treatment process, a device that does not include a dilator tip is also within the scope of the present invention.

The invention is not limited to the particular design of the device 100 shown in figures and variations in shape, size and configuration are within the scope of the invention.

In one or more embodiments, the device 100 may be manufactured in multiple colors. Each color may be associated with a particular size or diameter of the pre-loaded plug. In yet another embodiment, the device 100 may include the diameter information for the plug proximate the plug inserter end 120. In other embodiments, the diameter information may be coupled with a color-coded system.

The device 100 may be sold in separately wrapped sterile or non-sterile packages. When sold as a sterile package, the device 100 may be sold as a sterile kit with two sealed trays each of which securely holds a single device 100 having a preloaded plug 140. The tray can have a barrier lid. The tray and the device 100 can be pre-sterilized using a suitable agent, such as, ethylene oxide. Ethylene oxide sterilization involves exposing the tray and device 100 to ethylene oxide gas under vacuum in a sealed chamber. The sterilization can ensure that a safe and sterile device 100 is provided to the eye care professional.

Figure 6A:
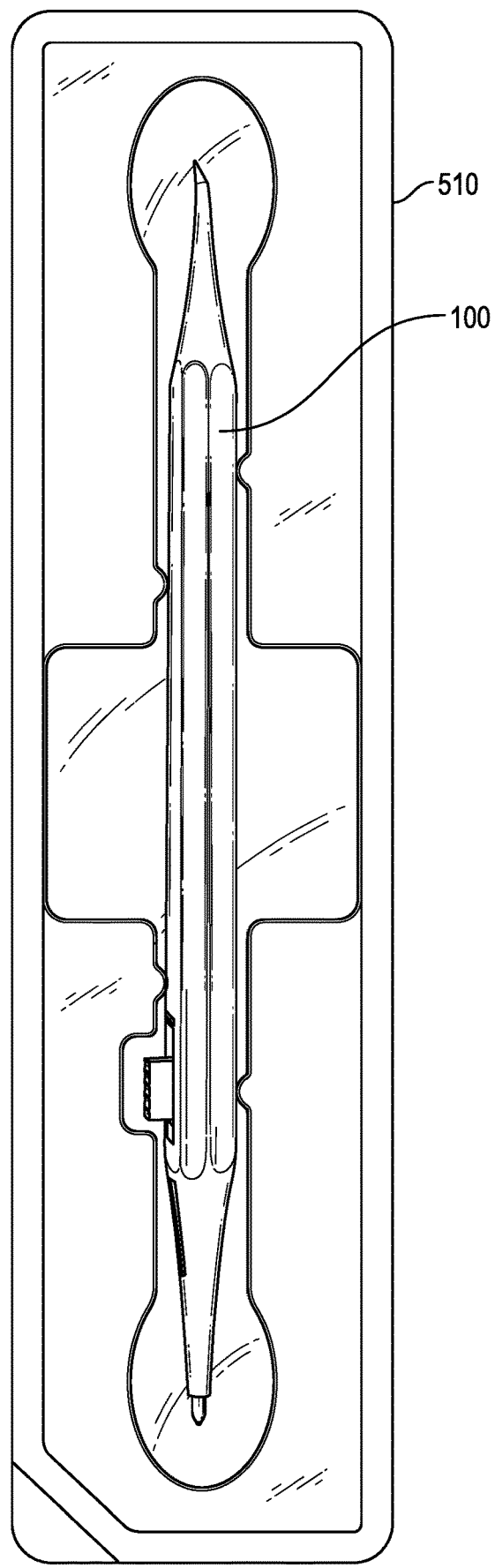
FIGS. 6A-6B illustrates a view of a kit according to an embodiment of the invention.
Figure 6B:
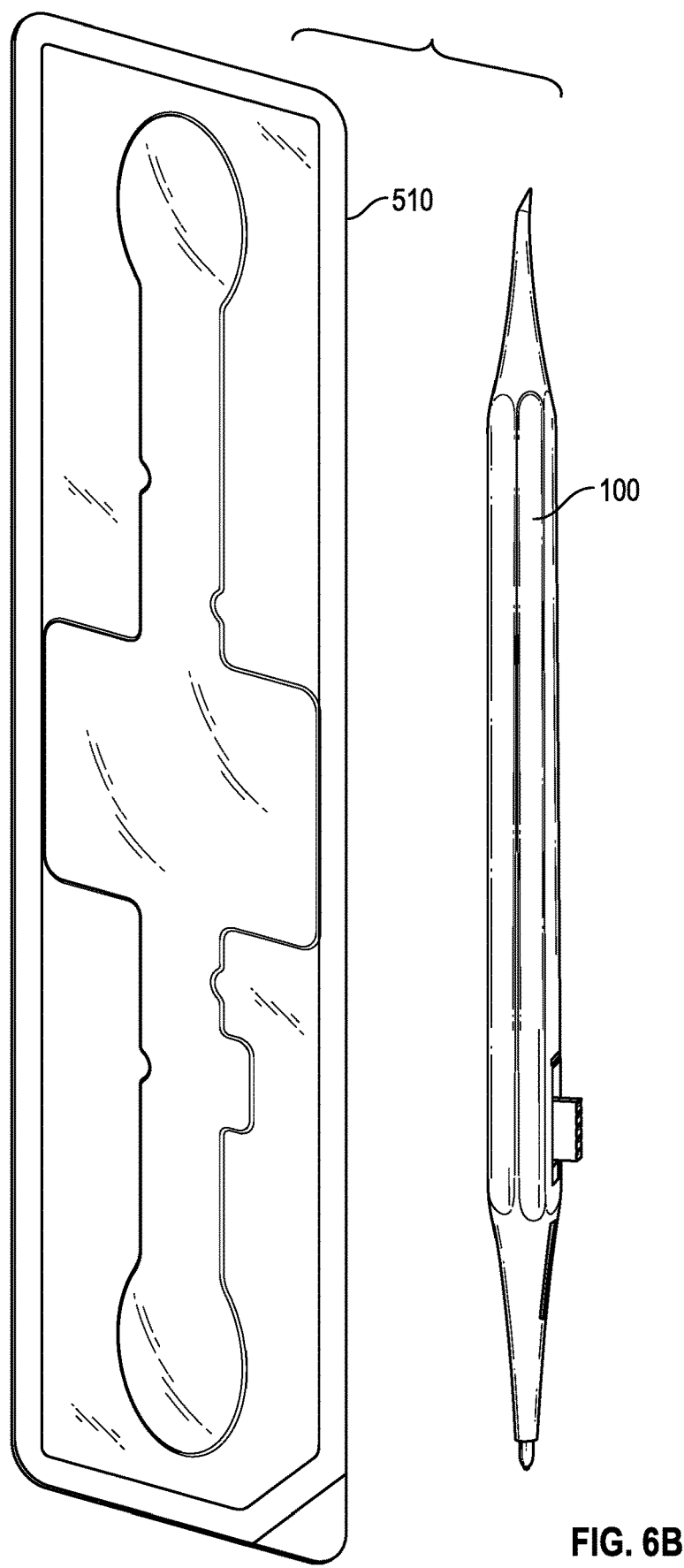

In one specific embodiment, as shown in FIGS. 6A and 6B, a kit 500 includes one or more sterile trays 510 each having a device 100 pre-loaded with a plug, and instructions for use ("IFU"). The one or more trays and the IFU can be vacuum sealed in a pouch. The pouch can then be positioned inside a container, such as, a box. The one or more trays and the box can include product indicia and other necessary information, such as, plug size, on its surface.

According to an embodiment, a method of assembling the device is disclosed. The method involves providing an intracanalicular plug (such as, plug 140). The plug may be a sterile or non-sterile plug which may be provided in a sealed pouch. The method further involves providing the body 110 of the device 100 disclosed herein. The method involves removing the plug from the pouch and mounting it in the channel 125B of the inserter tip 125. This may be followed by snapping on the plug ejector 200 to the body 110 such that the tip of the rod abuts one end of the plug and the other end of the plug protrudes out of the opening of the inserter tip. The method then involves compressing the cap on the inserter tip to hold the plug securely in position on the device 100. The device 100 is then sealed in a pre-molded tray/container with a sterile barrier lid. The tray and the device 100 can be sterilized using ethylene oxide.

According to another embodiment, a method of treating dry eyes is disclosed herein. The method involves providing a device 100 pre-loaded with an intracanalicular plug, as disclosed herein. The method involves removal of the protective cap from the inserter tip. An eye doctor can then position the device such that the inserter tip faces the patient's punctum. The inserter tip is then inserted into the canaliculus. This is followed by gently depressing the button and then moving the button forward toward the inserter tip. This causes the rod to eject the plug out of the opening at the inserter tip and into the canaliculus. The eye doctor can use the dilator end of the device 100 to further push the plug into a desired position inside the canaliculus.

A punctal diameter of 0.5 mm is common in many patients. In some embodiments, the eye doctor may use the dilator end of the device 100 to dilate the punctum prior to inserting the inserter tip into the canaliculus. This allows for easier insertion of the plug. However, in certain embodiments, the dilation step may be optional. Once the punctum is dilated, the doctor can turn the device 180° such that the inserter tip is facing the patient's punctum to insert the pre-loaded plug into the canaliculus.

The embodiments of the invention involve a single step insertion process since the plug is already pre-loaded in the device. The device 100 conveniently does not involve the use of any wires to release the plug. Further, the assembly of the inserter does not involve any adhesives or epoxy. The various components, such as, the plug and cap can snap together to make it a fully functional inserter too. Conveniently, the device 100 can be configured to accommodate plugs of different sizes.

The device 100 may be used by eye care doctors and professionals, such as, ophthalmologists, optometrists and other healthcare professionals. The device 100 is a medical device that may require a prescription. The one or more embodiments of the invention allow an eye doctor to perform the functions of dilating the punctum and inserting the punctum plug utilizing a unitary or single device. The device may be handheld and may be capable of being manipulated with one hand by the eye doctor, thereby ensuring convenience and efficiency. The utilization of a single apparatus may also result in cost-savings which may ultimately be passed down to the patients.

While the invention has been described in connection with a preferred embodiment, it is not intended to limit the scope of the invention to the particular form set forth, but on the contrary, it is intended to cover such alternatives, modifications, and equivalents as may be within the spirit and scope of the invention.

The invention claimed is:

1. An intracanalicular plug inserter device, comprising:
   (a) an elongate body having a longitudinal axis, the elongate body having:
      an inserter end, the inserter end having an opening therein; and
      a distal end, the distal end longitudinally opposing the inserter end; and
   (b) a plug ejector, wherein the plug ejector comprises:
      a slider; and
      a rod coupled to a first end of the slider,
   wherein the plug ejector is configured to be moveable between a first position adjacent to the opening in the inserter end and a second position that is further from the opening, wherein a plug is mounted within the elongate body, wherein the plug abuts a first end of the rod adjacent the opening in the inserter end; and wherein the plug ejector further includes a depressible button having a first side protruding outside of the elongate body and a second side mounted on the slider, wherein the second side of the depressible button comprises a pair of legs which are clipped to a first arm of the slider.

2. The device of claim 1, wherein the rod is configured to eject the plug from the opening in the inserter end when the first end of the slider is moved toward the inserter end.

3. The device of claim 1, further comprising a removable cap fitted to cover the plug and mounted at the inserter end of the elongate body.

4. The device of claim 1, further comprising a fine tip disposed at the distal end of the elongate body, wherein the fine tip is configured for dilating a lacrimal punctum.

5. The device of claim 4, wherein the depressible button is substantially locked in a first position by a protrusion and an indentation located on the first arm of the slider.

6. A kit comprising:
   the intracanalicular plug inserter device of claim 1;
   a tray for receiving the device; and
   instructions for using the device.

7. A method of treating dry eyes, comprising:
   providing the intracanalicular plug inserter device of claim 1;
   inserting the inserter end into a patient's canaliculus; and
   actuating the plug ejector to cause the plug to be ejected out of the opening at the inserter end.

8. The method of claim 7, further comprising dilating the patient's punctum prior to inserting the plug.

9. The method of claim 8, further comprising using the distal end of the device to push the plug further into the canaliculus.

* * * * *